(12) United States Patent
Butkevica

(10) Patent No.: US 11,529,221 B2
(45) Date of Patent: Dec. 20, 2022

(54) METHOD OF PREPARING A BONE SITE FOR RESTORATION PROCEDURE

(71) Applicant: Alena Butkevica, Huntington, NY (US)

(72) Inventor: Alena Butkevica, Huntington, NY (US)

( * ) Notice: Subject to any disclaimer, the term of this patent is extended or adjusted under 35 U.S.C. 154(b) by 413 days.

(21) Appl. No.: 16/857,816

(22) Filed: Apr. 24, 2020

(65) Prior Publication Data

US 2020/0345470 A1   Nov. 5, 2020

Related U.S. Application Data

(60) Provisional application No. 62/840,745, filed on Apr. 30, 2019.

(51) Int. Cl.
| | | |
|---|---|---|
| *A61C 17/20* | (2006.01) | |
| *A61K 49/00* | (2006.01) | |
| *A61C 3/02* | (2006.01) | |
| *A61C 8/00* | (2006.01) | |
| *A61F 2/46* | (2006.01) | |
| *A61C 8/02* | (2006.01) | |

(52) U.S. Cl.
CPC ............... *A61C 17/20* (2013.01); *A61C 3/02* (2013.01); *A61C 8/0012* (2013.01); *A61F 2/4601* (2013.01); *A61K 49/006* (2013.01); *A61C 8/00* (2013.01); *A61C 8/0006* (2013.01); *A61F 2002/4649* (2013.01)

(58) Field of Classification Search
CPC .. A61C 17/20; A61C 3/02; A61C 8/00; A61C 8/0012; A61C 8/0006; A61F 2/4601; A61F 2002/4649; A61F 2002/2835; A61K 49/006
USPC ........................................................ 606/86 r
See application file for complete search history.

(56) References Cited

U.S. PATENT DOCUMENTS

| | | | | |
|---|---|---|---|---|
| 5,954,996 A | * | 9/1999 | Discko, Jr. .......... | A61M 35/003 252/79.4 |
| 2009/0304622 A1 | * | 12/2009 | Meyer-Lueckel ..... | A61K 6/887 525/353 |

OTHER PUBLICATIONS

Pinheiro, S.L., Segatti, B., Pucca, D.S. et al. Dental acid etchantas a sensitizing agent in photodynamic therapy to reduce S. mutans in dentinal carious lesions. Lasers Med Sci 34, 305-309 (2018). https://doi.org/10.1007/s10103-018-2590-x; last accessed on Sep. 14, 2022 (Year: 2018).*

* cited by examiner

*Primary Examiner* — Marcela I. Shirsat
(74) *Attorney, Agent, or Firm* — Olson & Cepuritis, Ltd.

(57) ABSTRACT

A predetermined bone site in a patient selected for restoration is exposed, contacted with an aqueous, methylene blue containing phosphoric acid solution for a time period of at least 3 minutes but no more than about 15 minutes, and thereafter cleansed ultrasonically to remove any bacteria that may be present. Preferred phosphoric acid concentration in the aqueous solution is about 37 percent by weight.

10 Claims, No Drawings

METHOD OF PREPARING A BONE SITE FOR RESTORATION PROCEDURE

CROSS-REFERENCE TO RELATED APPLICATIONS

This application claims the benefit of U.S. Provisional Application Ser. No. 62/840,745, filed on Apr. 30, 2019, which is incorporated herein by reference in its entirety.

FIELD OF INVENTION

This invention relates to the preparation of a bone site for treatment of infected and/or osteoporotic bone with an immediate site reconstruction.

BACKGROUND OF INVENTION

Bone infection especially related to antibiotic resistant bacteria, resorption, bone loss, and osteoporosis are common, bone related problems. Infection and osteomyelitis represent significant complications of dental orthopaedic surgery. Infection rate with total hip and knee arthroplasty have been reported to be 0.88% and 0.92%, respectively, and resulting in substantial morbidity. It is estimated that by 2030 as many as 3.48 million knee replacements will take place in the United States with infection increase to 3%. Infection rates of open fractures range from several percentage to a staggering 50%. Implant associated osteomyelitis inflicts significant morbidity and mortality rate to the patient and proves a notable challenge for the orthopaedic surgeon. Antibiotic resistant bacteria's account for 65-80% of infection. Each year in the U.S. at least 2 million people become infected with bacteria that are resistant to antibiotics. Treatment of these infections experience longer hospital stays, require prolonged antibiotic therapy and experience 2.7 fold increase in mortality compared to non-infectious inpatients.

*Staphylococcus aureus* (*S. aureus*) osteomyelitis is a particularly significant complication for orthopedic patients undergoing surgery, particularly with fracture fixations, arthroplasty and open wound trauma. Patients with methicillin-resistant *Staphylococcus aureus* (MRSA) have longer hospital stays, require prolonged antibiotic therapy, and experience a 2.7 fold increase in mortality compared to non-infected hospital patients. One estimate of mean cost attributable to a MRSA infection is $35,367. The annual cost to treat hospitalized patients in the USA was estimated to be between $3.2B and 4.2B in 2000. Total hip and knee replacements are projected to grow between 174% and 673% during the next 20 years in the United States. Additionally, the infection rate after total knee replacement is reported to be 3% of the total procedures performed in the United States increasing in time. It has been estimated that 65% of injuries that occur during military combat are orthopedic in nature with up to 15% of those injuries developing osteomyelitis.

Total Medicare spending estimates for all wound types ranged from $28.1 to $96.8 billion. Including infection costs, the most expensive estimates were for surgical wounds ($11.7, $13.1, and $38.3 billion), followed by diabetic foot ulcers ($6.2, $6.9, and $18.7 billion,). The highest cost estimates in regard to site of service were for hospital outpatients ($9.9-$35.8 billion), followed by hospital inpatients ($5.0-$24.3 billion).

In the field of dentistry, the number of bone grafts and dental implants performed has doubled in the past five years. About 9,000,000 dental implants were inserted in 2018 in the United States alone, and the number of implants keeps increasing. Bone loss related to the teeth infections creates additional bone restorative (bone grafting) surgeries, which are less predictable. Bone grafting is a procedure that is sometimes required after tooth extraction and before or during dental implant the placement of a dental implant can cause complications appear to be chronic pain in a range of 2.5% from 8% of cases, dysesthesia in 6% of cases, or infection in 2% of cases.

The main purpose of bone grafting is to preserve or increase the amount of bone that is present at the implant or surgical site.

Problems associated with bone grafts and dental and orthopaedic implants include immunological rejection, infections at surgery sites, morbidity related to autogenous bone placement, anesthesia side effects, post-surgical complications, repeated surgeries requiring antibiotic intake, as well as economic costs. Infections resorb bone, and current treatment modality is to cut back, which leads to even greater bone loss. Also, bone grafting material generally tends to resorb as much as 55 percent within the first year after the procedure.

The present method of bone site preparation ameliorates the aforementioned problems and facilitates simultaneous bone grafting and implant placement leading to long term success with minimal or substantially no bone resorption.

SUMMARY OF INVENTION

A method for preparing a bone site of a patient for a bone restoration procedure comprises debriding the infected bone site, contacting the debrided bone site, immediately prior to the procedure, with an aqueous, methylene blue containing phosphoric acid ($H_3PO_4$) solution for a time period of at least 3 minutes but no more than about 15 minutes, preferably about 5 to 10 minutes. The phosphoric acid solution can be applied to the exposed bone site as an acid gel etch or a liquid etchant. The concentration of phosphoric acid in the applied solution can vary, but preferably is in the range of about 20 to about 40 percent by weight. More preferably, the phosphoric acid concentration is about 37 percent by weight. Thereafter, the bone site is rinsed with saline until all phosphoric acid has been removed from the bone site and the bone site exhibits a distinctive gray color. After the rinsing step the bone site is cleansed with ultrasound until the bone site no longer has gray coloration but appears yellow to white in color. The so treated bone site is then ready for restoration. To promote healing, bleeding can be induced at the treated bone site drilling small holes in the bone to access bone marrow.

DESCRIPTION OF PREFERRED EMBODIMENTS

Preparation of a patient's bone site for a bone restoration procedure such as a bone graft and/or an implant, and/or bone density increase comprises the steps of:

(A) exposing the bone site;
(B) contacting the exposed bone site with an aqueous phosphoric acid solution that contains methylene blue until bone surface porosity can be seen upon visual inspection, usually for a time period of at least 3 minutes, preferably about 5 to 10 minutes, but no more than about 15 minutes;
(C) thereafter removing any phosphoric acid present at the exposed bone site by rinsing the bone site with a saline solution for a time period sufficient to remove any phosphoric acid therefrom; and (D) ultrasonically cleaning the bone site until the bone site appears yellow to white in color.

For a bone graft, the foregoing method of preparation is followed by a further step of creating an opening at the bone site to provide access to bone marrow. This opening can be created by drilling under a saline rinse and the like procedure.

In particular, a preferred method of placing a bone graft at the bone site comprises performing Step (A) through (D) described hereinabove, then (E) creating at least one access opening at the bone site sufficient to provide access to bone marrow, (F) introducing grafting material into the opening, and thereafter (G) closing the exposed bone site by suturing with an absorbable suture. A resorbable membrane may be used to cover the bone site to prevent soft tissue ingrowth. The bone grafting material can be autologous (or autogenous), allograft, xenograft, or synthetic such as hydroxyapatite and the like. Mixtures of the grafting material can be used as well. A particularly preferred bone grafting material is a mixture of autologous bone obtained from the surgical site with hydroxyapatite.

Phosphoric acid applied to exposed bone at the surgical site hardens the bone and promotes osteogenesis. For the purposes of the present method of preparation of the implant or bone graft site, the concentration of phosphoric acid is in the range of about 20 percent to about 40 percent by weight. A phosphoric acid concentration of about 37 weight percent is preferred. The phosphoric acid together with methylene blue also serves as an indicator for bacteria. A color change from blue to gray indicates presence of bacteria at the bone site. Any bacteria present at the bone site are removed by the ultrasonic cleansing.

The ultrasonic cleansing can be done using an ultrasonic cleaning machine such as a dental ultrasonic cleaner having a frequency output in the range of about 25 kHz to about 60 kHz, preferably 45 kHz at an intensity of about 30 mW/cm$^2$. Ultrasonic cleansing further aids in the reduction of bacterial contamination as well as induces proliferation of fibroblasts and osteoblasts.

The absorbable suture preferably is a polyglycolic acid suture such as the absorbable, synthetic braided suture commercially available under the designation VICRYL from Ethicon, Inc., New Jersey, U.S.A.

A dental orthopedic implant can be made at the exposed bone site in a similar manner. The implant is positioned into the access opening concurrently with introduction of the bone graft material into the bone marrow and thereafter closing the site by loosely placed gingiva and suturing with an absorbable suture.

The aforedescribed method provides the following advantages:

(1) reduction in the number of surgeries required;
(2) only very mild post-operative pain is experienced by the patient;
(3) minimal swelling;
(4) reduction in amount of antibiotic administered to the patient;
(5) elimination of need for general anesthesia;
(6) absence of immunological reactions;
(7) implant and bone graft material can be placed into an infected extraction pocket concurrently after thorough debridement;
(8) substantial reduction in time for healing and restoration (usually from 12+ months to 4 months or less);
(9) reduction in surgery time and attendant costs to the patient.

The foregoing description is illustrative and is not to be taken as limiting. Still other variants of the procedure are within the spirit and scope of the present invention and will readily present themselves to those skilled in the art.

I claim:

1. A method of preparing a bone site in a patient for a bone restoration procedure which comprises exposing the bone site and contacting the exposed bone site, immediately prior to the dental procedure, with an aqueous, methylene blue containing phosphoric acid solution for a time period of at least 3 minutes but no more than 15 minutes, removing the phosphoric acid solution, and thereafter ultrasonically cleansing the exposed bone site.

2. A method of preparing a bone site in a patient for a bone restoration procedure which comprises the steps of:
   (A) exposing the bone site;
   (B) contacting the exposed bone site with an aqueous, methylene blue containing phosphoric acid solution for a time period of at least 3 minutes but no more than 15 minutes;
   (C) thereafter removing any phosphoric acid present by rinsing the exposed bone site with a saline solution for a time period sufficient to remove any phosphoric acid therefrom; and
   (D) ultrasonically cleansing the exposed bone site.

3. The method in accordance with claim 2 wherein the bone restoration procedure is a bone graft.

4. The method in accordance with claim 2 wherein the bone restoration procedure is placement of a dental implant.

5. The method in accordance with claim 2 wherein the aqueous phosphoric acid solution contains 30 to 40 percent by weight phosphoric acid and the ultrasonic cleansing is effected at a frequency in the range of about 25 kHz to about 60 kHz.

6. The method in accordance with claim 2 wherein the aqueous phosphoric acid solution contains 37 percent by weight phosphoric acid.

7. The method in accordance with claim 2 including a further step of creating an opening at the bone site providing access to bone marrow.

8. The method in accordance with claim 7 wherein the opening is created by drilling under a saline rinse.

9. A method of placing a bone graft which comprises the steps of:
   exposing the bone site;
   contacting the exposed bone site with an aqueous, methylene blue containing phosphoric acid solution for a time period of at least 3 minutes but no more than 15 minutes;
   thereafter removing any phosphoric acid present by rinsing the exposed bone site with a saline solution for a time period sufficient to remove any phosphoric acid therefrom;
   ultrasonically cleansing the exposed bone site;
   creating an opening at the bone site sufficient to access bone marrow;
   introducing grafting material into the opening; and
   closing the exposed bone site by positioning gingiva over the bone site and securing the gingiva by suturing with an absorbable suture.

10. The method in accordance with claim 9 wherein the absorbable suture is a polyglycolic acid suture.

* * * * *